US011666219B2

(12) United States Patent
Fox

(10) Patent No.: US 11,666,219 B2
(45) Date of Patent: Jun. 6, 2023

(54) METHODS AND APPARATUS FOR NETWORK LOCALIZATION OF NEUROLOGICAL SYMPTOMS FROM FOCAL BRAIN LESIONS

(71) Applicant: Beth Israel Deaconess Medical Center, Inc., Boston, MA (US)

(72) Inventor: Michael D. Fox, Brookline, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 386 days.

(21) Appl. No.: 16/321,688

(22) PCT Filed: Jul. 28, 2017

(86) PCT No.: PCT/US2017/044488
§ 371 (c)(1),
(2) Date: Jan. 29, 2019

(87) PCT Pub. No.: WO2018/023056
PCT Pub. Date: Feb. 1, 2018

(65) Prior Publication Data
US 2020/0352443 A1    Nov. 12, 2020

Related U.S. Application Data

(60) Provisional application No. 62/368,933, filed on Jul. 29, 2016.

(51) Int. Cl.
*A61B 5/00* (2006.01)
(52) U.S. Cl.
CPC .......... *A61B 5/0042* (2013.01); *A61B 5/4064* (2013.01); *A61B 5/7425* (2013.01)
(58) Field of Classification Search
CPC ... A61B 5/0042; A61B 5/4064; A61B 5/7425; A61B 5/0507; A61B 5/0515;
(Continued)

(56) References Cited

U.S. PATENT DOCUMENTS

| | | | |
|---|---|---|---|
| 6,430,430 B1 * | 8/2002 | Gosche | G06T 7/0012 600/410 |
| 2004/0092809 A1 * | 5/2004 | DeCharms | A61B 5/4088 600/410 |

(Continued)

OTHER PUBLICATIONS

International Search Report and Written Opinion for International Application No. PCT/US2017/044488 dated Oct. 12, 2017.
(Continued)

*Primary Examiner* — Joseph M Santos Rodriguez
*Assistant Examiner* — Kaitlyn E Sebastian
(74) *Attorney, Agent, or Firm* — Wolf, Greenfield & Sacks, P.C.

(57) ABSTRACT

Methods and apparatus for providing a functional mapping of a brain lesion in a patient's brain. The method comprises determining using a computer processor, based on human connectome data stored on at least one computer datastore in communication with the computer processor, at least one functional network associated with a location of a brain lesion identified in an image of a patient's brain. The at least one functional network includes a plurality of brain areas functionally connected to the location of the brain lesion and a plurality of correlation measures. Each of the correlation measures indicates a strength of functional connection between the location of the brain lesion and a respective brain area of the plurality of brain areas in the at least one functional network. The method further comprises determining, based at least one functional network, a likelihood that the brain lesion is causing one or more patient symptoms.

23 Claims, 9 Drawing Sheets

(58) Field of Classification Search
CPC ..... A61B 5/055; A61B 5/7246; A61B 5/7264; G06T 7/0012; G06T 2207/10088; G06T 2207/30016

See application file for complete search history.

(56) References Cited

U.S. PATENT DOCUMENTS

| | | | |
|---|---|---|---|
| 2007/0043401 A1 | 2/2007 | John | |
| 2011/0004412 A1 | 1/2011 | Shahaf et al. | |
| 2011/0270348 A1* | 11/2011 | Goetz | A61N 1/36135 607/45 |
| 2012/0296569 A1 | 11/2012 | Shahaf et al. | |
| 2015/0272468 A1* | 10/2015 | Liu | A61B 5/055 600/410 |
| 2016/0019693 A1* | 1/2016 | Silbersweig | G16H 50/20 382/128 |
| 2016/0136427 A1 | 5/2016 | De Ridder | |
| 2016/0279380 A1 | 9/2016 | Metzger | |
| 2017/0039708 A1* | 2/2017 | Henry | A61B 5/4848 |

OTHER PUBLICATIONS

International Preliminary Report on Patentability for International Application No. PCT/US2017/044488 dated Feb. 7, 2019.

[No Author Listed], MNI ICBM 152 non-linear 6th Generation Symmetric Average Brain Stereotaxic Registration Model. 2019. 2 pages, http://nist.mni.mcgill.ca/?p=858 [last accessed date Apr. 29, 2019].

[No Author Listed], Mricron v2.1.46-1. 5 pages, https://www.nitrc.org/projects/mricron [last accessed dated Apr. 29, 2019].

[No Author Listed], Nonparametric mapping software. http://www.mccauslandcenter.sc.edu/mricro/npm. Wayback Machine https://web.archive.org/web/20151207035940/http://www.mccauslandcenter.sc.edu/mricro/npm [last accessed date Apr. 26, 2019]. 2 pages.

Boes et al., Network localization of neurological symptoms from focal brain lesions. Brain. Oct. 2015;138(Pt 10):3061-75. doi:10.1093/brain/awv228.

Darby et al., Finding the imposter: brain connectivity of lesions causing delusional misidentifications. Brain. Feb. 2017;140(2):497-507. doi:10.1093/brain/aww288.

Darby et al., Reply: Capgras syndrome: neuroanatomical assessment of brain MRI findings in an adolescent patient. Brain. Jul. 1, 2017;140(7):e44. doi:10.1093/brain/awx125.

Fasano et al., Lesions causing freezing of gait localize to a cerebellar functional network. Ann Neurol. Jan. 2017;81(1):129-141. doi:10.1002/ana.24845. [Author Manuscript].

Fischer et al., A human brain network derived from coma-causing brainstem lesions. Neurology. Dec. 6, 2016;87(23):2427-2434.

Fox et al., The human brain is intrinsically organized into dynamic, anticorrelated functional networks. Proc Natl Acad Sci U S A. Jul. 5, 2005;102(27):9673-8.

Laganiere et al., Network localization of hemichorea-hemiballismus. Neurology. Jun. 7, 2016;86(23):2187-95.doi:10.1212/WNL.0000000000002741.

Van Dijk et al., Intrinsic functional connectivity as a tool for human connectomics: theory, properties, and optimization. J Neurophysiol. Jan. 2010;103(1):297-321. doi: 10.1152/jn.00783.2009.

\* cited by examiner

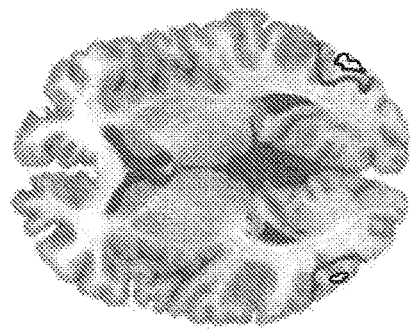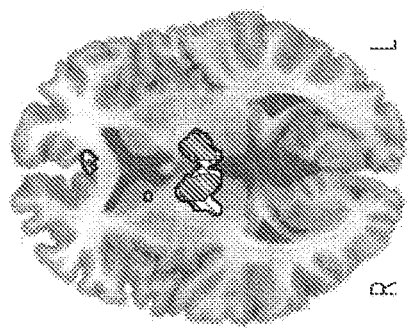
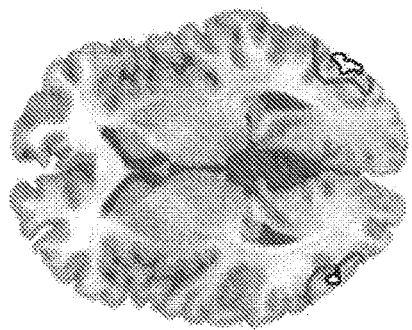
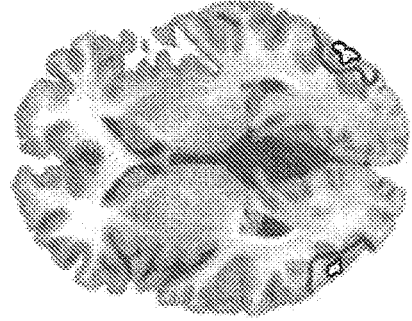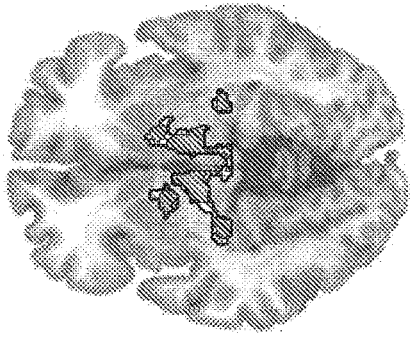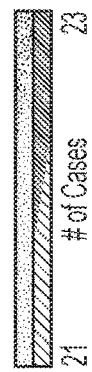
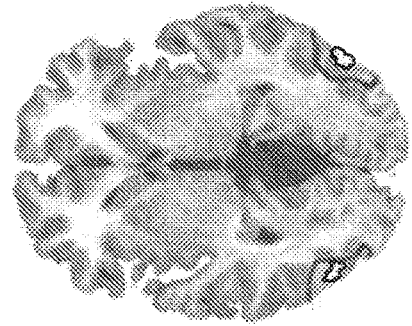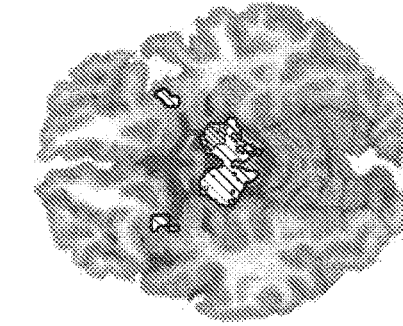
FIG. 4A
FIG. 4B

METHODS AND APPARATUS FOR NETWORK LOCALIZATION OF NEUROLOGICAL SYMPTOMS FROM FOCAL BRAIN LESIONS

CROSS-REFERENCE TO RELATED APPLICATIONS

This Application is a national stage filing under 35 U.S.C. § 371 of International Patent Application Serial No. PCT/US2017/044488, filed Jul. 28, 2017, which claims the benefit under (35 USC 119(e) of U.S. Provisional Application Ser. No. 62/368,933, filed Jul. 29, 2016, and entitled "METHODS AND APPARATUS FOR NETWORK LOCALIZATION OF NEUROLOGICAL SYMPTOMS FROM FOCAL BRAIN LESIONS," the entire contents of these applications are incorporated herein by reference in their entirety.

FEDERALLY SPONSORED RESEARCH

This invention was made with government support under grant NS065743 awarded by NIH. The government has certain rights in the invention.

BACKGROUND

There is a long tradition of understanding regional brain function by studying deficits that result from focal brain injury. An examination of patients with similar symptoms that have lesions overlapping in a specific brain region provides insight into the functional role of that region. Because this lesion mapping approach requires only a record of patient symptoms and the location of the lesion, it has proven broadly applicable across many neurological and psychiatric symptoms. Methodological improvements using statistics to identify critical sites of lesion overlap have further enhanced the utility of this approach.

SUMMARY

The standard in the field of clinical neuroimaging of brain lesions involves detecting a lesion using structural magnetic resonance imaging (MRI). The lesion site is visualized and no further information is gathered. The inventors have recognized that conventional lesion analysis that considers only the location of the lesion may be improved by leveraging normative human connectome data to not only show the site of injury, but also the network of regions predicted to be affected by the lesion. Identifying target brain areas functionally connected to the lesion site and implicated for a patient's condition may result in improved prognostication so the patient can plan for their level of disability and recovery, predict the onset of delayed stroke syndromes such as post stroke pain or depression, and provide useful information to guide therapy such as what type of rehabilitation is likely to be helpful.

The lesion network mapping technique described herein leverages normative human connectome databases to predict network effects in patients. Examples include predicting symptoms, cortical atrophy in stroke patients, atrophy progression in patients with neurodegenerative disease, effects of focal brain stimulation, and lesion-induced connectivity changes based on computational modeling. As described in more detail below, some embodiments use connectome databases to predict the network effects of focal brain lesions using functional connectivity MRI. Because network effects of brain lesions can impact prognosis or be used to guide therapy, these approaches may represent clinical applications of the human connectome project.

Some embodiments are directed to a method for identifying at least one target site for treatment. In some embodiments, the treatment may be treatment using non-invasive brain stimulation. The standard approach for identifying a target site for non-invasive brain stimulation in rehabilitation from a brain lesion, such as a stroke, involves selecting a target brain region and using the same target brain region for all patients with a given symptom, regardless of lesion location. For example, if the patient has weakness on one side of the body the motor cortex may be targeted on the same side as the patient's weakness. The lesion site is not taken into account. Some embodiments determine a set of one or more brain regions as target(s) for non-invasive brain stimulation treatment. Individualizing the treatment based on brain regions predicted to be affected by the lesion may improve outcomes, as these are the sites most likely to undergo compensatory changes to aid in recovery. In some embodiments, the non-invasive brain stimulation comprises transcranial magnetic stimulation (TMS). In other embodiments, the non-invasive brain stimulation comprises one or more of transcranial direct current stimulation (tDCS), pulsed ultrasound, and radiation (e.g., light) therapy.

In some embodiments, the treatment may include use of a medication known to target the brain regions(s) or networks identified using one or more of the techniques described herein. In other embodiments, the treatment may include rehabilitation and/or physical strategies, use of injectable substances such as growth factor or gene therapies, invasive stimulation an example of which includes, but is not limited to, deep brain stimulation.

Some embodiments are directed to a magnetic resonance imaging (MRI) system configured to acquire one or more images of a patient. The MRI system includes at least one processor programmed to process the one or more acquired images to identify at least one lesion and to perform lesion network mapping to generate predicted network effects of the detection lesion. In some embodiments the MRI system may be further configured to present the predicted network effects as a visualization on an image of a patient's brain and/or by providing prognostically useful text to aid treatment. For example, the text may state that the lesion site has remote effects on language and pain regions and has an 85% chance of resulting in a delayed pain syndrome. Medical personnel may use the predications to guide treatment of the patient and/or perform more tests on the patient.

Some embodiments are directed to a method of determining a set of target brain regions for treatment. The method comprises mapping a lesion site to a reference brain, assessing functional connectivity of the lesion using human connectome data stored in a database to determine the set of target brain regions, and outputting the set of target brain regions.

Some embodiments are directed to a method of identifying at least one brain region associated with one or more patient symptoms of a medical condition. The method comprises determining based, at least in part, on normative human connectome data, a functional network for a brain lesion identified in an image of the patient's brain, wherein the at least one brain region is determined based, at least in part, on the determined functional network. In some embodiments, determining the functional network comprises selecting a region of interest (ROI) based, at least in part, on the medical condition and/or the symptoms of the medical condition.

Some embodiments are directed to a computer-readable storage medium encoded with a plurality of instructions that, when executed by at least one computer processor perform a method of determining a set of target brain regions for treatment. The method comprises mapping a lesion site to a reference brain, assessing functional connectivity of the lesion using human connectome data stored in a database to determine the set of target brain regions, and outputting the set of target brain regions. In some embodiments, outputting the set of target brain regions comprises outputting coordinates of the brain region(s) in the set, wherein the coordinates are in a standardized coordinate space.

Some embodiments are directed to a method of receiving, from an MRI system, at least one image of a patient on which a lesion has been identified, determining a functional connectivity map for the lesion based, at least in part, on one or more of patient symptoms, a medical condition of the patient, and normative human connectome data, and guiding a treatment of the medical condition of the patient based, at least in part, on the functional connectivity map.

Some embodiments are directed to a method of determining a functional connectivity map for a lesion in a patient's brain without requiring functional neuroimaging from the patient. The method comprises determining the functional connectivity map based, at least in part, on normative resting state functionally connectivity MRI data to identify brain regions likely to be affected by a brain lesion.

Some embodiments are directed to a method of predicting one or more current and/or future symptoms caused by a lesion. Such predictions may include a prognosis for recovery. Some embodiments are directed to a method of assessing the likely effectiveness of candidate pharmaceuticals targeted to the one or more predicted symptoms for individual patients.

Some embodiments are directed to a method of providing a functional mapping of a brain lesion in a patient's brain. The method comprises determining using a computer processor, based on human connectome data stored on at least one computer datastore in communication with the computer processor, at least one functional network associated with a location of a brain lesion identified in an image of a patient's brain. The at least one functional network includes a plurality of brain areas functionally connected to the location of the brain lesion and a plurality of correlation measures. Each of the correlation measures indicates a strength of functional connection between the location of the brain lesion and a respective brain area of the plurality of brain areas in the at least one functional network. The method further comprises determining, based on the at least one functional network, a likelihood that the brain lesion is causing one or more patient symptoms.

Some embodiments are directed to a system for providing a functional mapping of a brain lesion in a patient's brain. The system comprises a magnetic resonance imaging (MRI) system configured to acquire one or more images of a patient's brain, a database configured to store human connectome data comprising resting state functional connectivity data, and at least one computer communicatively coupled to the MRI system and the database. The at least one computer comprises a computer processor configured to perform the acts of: receiving the one or more images from the MRI system, identifying a location of a brain lesion from the one or more images; determining, based on the human connectome data and the identified location of the brain lesion, a functional connectivity map associated with the location of the brain lesion, wherein the functional connectivity map includes a plurality of brain areas functionally connected to the location of the brain lesion and a plurality of correlation measures, wherein each of the correlation measures indicates a strength of functional connection between the location of the brain lesion and a respective brain area of the plurality of brain areas in the functional connectivity map, and determining, based on the at least one functional network, a likelihood that the brain lesion is causing one or more patient symptoms.

The foregoing summary is provided by way of illustration and is not intended to be limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 4A and 4B show results of applying a lesion network mapping process to peduncular hallucinosis lesions in accordance with some embodiments;

DETAILED DESCRIPTION

Figure 1:
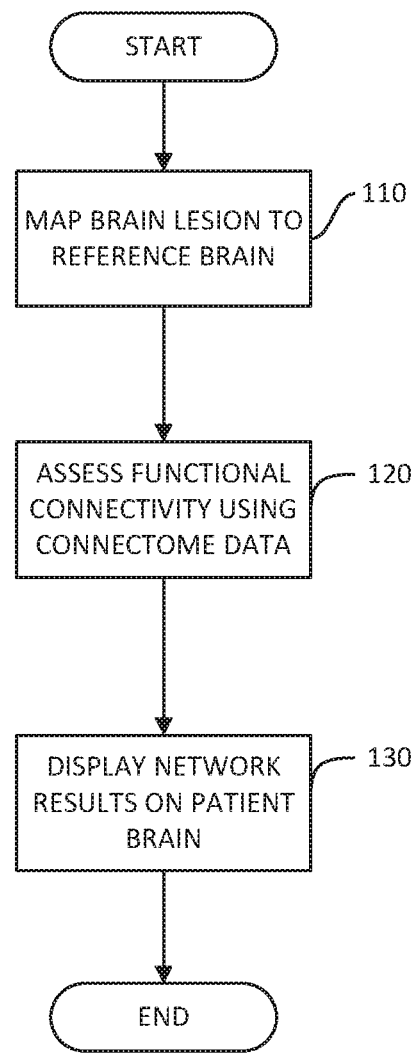
FIG. 1 is a flowchart of a lesion network mapping process in accordance with some embodiments.

Some traditional approaches to lesion mapping are limited by two important factors. First, similar symptoms may result from lesions in different locations, making localization to specific regions challenging. Second, symptoms may result from lesion-induced functional alterations in anatomically intact, connected brain regions. The fact that lesions have remote functional effects has been appreciated for over a century; however, it has remained unclear how one might incorporate such effects into traditional lesion mapping. One solution for localizing neurological symptoms that incorporates such network effects is to perform functional imaging on patient cohorts with brain lesions. This approach has firmly established the importance of remote network effects in symptom expression and recovery of function, but requires specialized functional neuroimaging scans, which are not routinely collected for clinical purposes. Obtaining such data is especially difficult for rare symptoms, transient symptoms, or conditions that render brain scanning difficult.

As such, many studies of lesion-induced neurological symptoms continue to rely solely on the analysis of lesion site for symptom localization. Some embodiments are directed to incorporating the network effects of brain lesions into traditional lesion mapping without the need for specialized brain imaging of patients. The techniques described herein, also referred to as "lesion network mapping," leverage normative human connectome data to identify the distribution of regions likely to be functionally affected by a given brain lesion. For each lesion, a lesion-derived network is identified using resting state functional connectivity MRI, which examines correlations in spontaneous, low frequency fluctuations of the blood oxygen level-dependent (BOLD) signal. In contrast to conventional techniques that collect resting state functional connectivity MRI in patients with brain lesions, some embodiments use a large normative resting state functional connectivity MRI database to identify regions likely to be affected by a brain lesion, without the need for specialized imaging of the patients.

In some embodiments, the human connectome data includes resting state functional connectivity data collected from a number of subjects. In other embodiments, the human connectome data includes data describing functional connections between brain areas as determined using another technique, examples of which include, but are not limited to, magnetoencephalography (MEG), electroencephalography (EEG), electrocorticography (ECoG) recordings, and MRI recordings in which data other than resting state functional connectivity data is collected. In embodiments in which the human connectome data includes resting state functional connectivity data, the resting state functional connectivity data is collected by examining spontaneous fluctuations in a subject's brain activity while the subject is in a resting state (e.g., lying down in an MRI scanner). Simultaneous activation of two or more brain areas/regions in the resting state data is indicative of a functional connection between the two or more brain areas.

The human connectome data is used in some embodiments to derive functional connectivity maps describing a set of functionally connected brain areas and strengths of functional connections between the brain areas in the set. For example, a functional connectivity map associated with a first brain area can include one or more other brain areas functionally connected to the first brain area. A functional connectivity map generated in accordance with the techniques described herein may also include correlation measures, each of which indicates a strength of a functional connection between two brain areas in the set of brain areas in the functional connectivity map. For instance, two brain areas in the set may be identified as being positively correlated when the human connectome data indicates that both areas showed an increase (or decrease) in activity at the same time, or as being or negatively correlated when the human connectome data indicates that one of the areas showed an increase in activity at the same time that the other area showed a decrease in activity. The strength of the negative or positive correlation between the brain areas in the functional connectivity map may be represented numerically, for example, with a value of $-1$ representing perfect negative correlation (i.e., increased activity in one area always resulted in simultaneously decreased activity in the other area), a value of 0 representing no correlation between the areas, and a value of 1 representing perfect positive correlation (i.e., both areas always showing simultaneous increased or decreased activity). For example, a correlation measure of 0.8 may indicate a strong positive correlation between the two brain areas, whereas a correlation measure of 0.1 may indicate a weaker positive correlation between the two brain areas. Similarly, a correlation measure of $-0.8$ may indicate a strong negative correlation between the two areas, whereas a correlation measure of $-0.2$ may indicate a weaker negative correlation between the two brain areas. Although a scale of $-1$ to 1 is described herein for representing a strength of correlation between two brain areas, it should be appreciated that any suitable numerical scale may alternatively be used, and embodiments are not limited in this respect.

Some databases of connectivity between brain areas focus on identifying structural (e.g., white matter connections) between the brain areas using, for example, diffusion tensor imaging (DTI)-based tractography. When used for lesion mapping, such structural connectivity information only identifies an immediate downstream region connected to the location of the brain area that includes the lesion. By contrast, resting state functional connectivity data, used in accordance with some embodiments, describes functional mappings that can be used to identify multiple brain areas to which the brain area including the lesion is directly or indirectly connected. That is, rather than just capturing monosynaptic structural connections between brain areas, the resting state functional connectivity data captures information associated with polysynaptic connections between different brain regions.

Additionally, information about the strength of a connection between two structurally-connected brain regions in structural connectivity data is typically limited to information about the size of the white matter tracks connecting the two brain regions, but does not take into consideration the extent to which neural signals are processed by the two brain regions. By contrast, resting state functional connectivity data describes both the amount and timing of neural activity arising in the brain regions, and as such information about the strength of the connections between the brain regions in a functional map may also be determined. The inventors have recognized that traditional lesion mapping, including techniques that use structural connectivity data, can be improved by leveraging resting state functional connectivity data that indicates functional consequences/effects of a brain lesion on other brain regions without the need for specialized brain imaging.

To demonstrate the utility of the approach, two main hypotheses were tested: (i) lesions that cause similar symptoms but occur in different locations will show overlap in network connectivity; and (ii) sites of network overlap will occur specifically in regions implicated in symptom expression. While not limited for use with any particular medical condition, experimental validation of the lesion network mapping technique described herein focused on peduncular hallucinosis, a neurological syndrome in which lesion-induced network effects are thought to play a pivotal role in generating symptoms. Peduncular hallucinosis is characterized by vivid, dynamic, well-formed visual hallucinations following a lesion to the pons, midbrain, or thalamus. Why visual hallucinations result from these lesions in non-visual structures remains unknown, but a 'release' of cortical activity in the extrastriate visual cortex, a region active during visual hallucinations, is thought to occur.

Analysis of patients with peduncular hallucinosis is thus well suited to a validation of the lesion network mapping technique. Specifically, lesion localization in peduncular hallucinosis is heterogeneous, symptoms are hypothesized to result from distributed network effects, and there is a clear a priori hypothesis regarding what remote site should be involved in symptom generation. In addition to peduncular hallucinosis, three other syndromes in which reasonable predictions regarding network effects could be made were also investigated: auditory hallucinosis, with network effects in the superior temporal gyrus; central post-stroke pain, with network effects in the posterior insula; and subcortical expressive aphasia, with network effects in Broca's area.

As discussed in more detail below, some embodiments demonstrate that (i) lesion sites that produce similar neurological symptoms but occur in different locations show overlap in their functional connectivity networks; (ii) this overlap occurs in regions hypothesized a priori to be involved in symptom expression; and (iii) these findings hold true across lesion syndromes. Together, these findings suggest that human connectome data can be used to incorporate network effects of brain lesions into symptom localization. Because the techniques described herein do not require advanced neuroimaging of patients, it may prove broadly applicable towards understanding the neural correlates of symptom expression across a variety of neurological and psychiatric syndromes.

The utility of some embodiments was demonstrated in a syndrome long hypothesized to be due to remote network effects, linking brainstem and thalamus lesions in peduncular hallucinosis to cortical areas implicated in visual release hallucinations. The generalizability of the technique was demonstrated by analyzing three additional disorders: auditory hallucinosis, central post-stroke pain, and subcortical expressive aphasia. As discussed further below, some embodiments help address limitations of traditional lesion mapping, offer complimentary information relative to functional imaging in patients, and provide unique insights into different lesion syndromes.

Augmenting the traditional approach, the lesion network mapping approach described herein addresses some limitations of traditional lesion mapping including (i) allowing for heterogeneously distributed lesions resulting in the same clinical syndrome to be grouped into a single unifying network; and (ii) linking lesions to remote brain regions with a more direct or more easily recognized role in the behavioral expression of the lesion. For example, as discussed in more detail below, lesions in patients with peduncular hallucinosis showed widespread distribution with overlap that spanned multiple regions, but most of the lesions localized to the same functional networks. Moreover, sites of lesion overlap that did occur in peduncular hallucinosis were not in visual areas, leaving it unclear how these sites relate to the symptom of visual hallucinations. In contrast, network overlap localized specifically to the extrastriate visual cortex, a region clearly implicated in visual hallucinations as demonstrated in prior functional neuroimaging studies of patients with peduncular hallucinosis.

Functional brain imaging in patients has been used to relate symptoms to the network effects of brain lesions. While similar in motivation, that approach is different and complimentary to the novel technique described herein. Functional brain imaging typically requires functional neuroimaging data to be collected on patients, whereas the techniques described herein do not require the collection of functional neuroimaging data. While there is clear value to direct measurement of neurophysiological effects in symptomatic patients, there is also value to increased versatility. The techniques described herein can be applied to almost any neurological syndrome based solely on lesion location. Additionally, post-lesion functional neuroimaging is not able to investigate the physiology or connectivity of the lesion location itself, as this tissue has been destroyed by the lesion. By contrast, some embodiments described herein investigate properties of the lesion location based on a cohort of intact subjects. Finally, functional neuroimaging abnormalities in patients likely represent a combination of direct lesion-induced functional changes and secondary compensatory responses. Combining functional neuroimaging with the techniques described herein may prove a powerful approach for differentiating direct versus compensatory processes (see discussion on central post-stroke pain below). The techniques described herein may also be used to identify a priori regions of interest in which to investigate the network effects of lesion patients undergoing functional imaging.

FIG. 1 illustrates a block diagram of process for determining a functional network based on an analysis of lesion locations in accordance with some embodiments. FIG. 1 depicts the lesion network mapping technique using functional connectivity information associated with the brain. In act 110, the location of a brain lesion for a patient is mapped to a reference brain. The reference brain may be a standardized brain such as included as part of FSL software available through Oxford University Oxford, UK, using lesion mapping software (e.g., MRIcron software, available through Mccausland Center for Brain Imaging, University of South Carolina, Columbia, S.C.), or using other suitable techniques or software. In some embodiments, the location of brain lesion may be mapped to the same reference brain as a normative dataset of human connectome data. In some embodiments, the lesion location is identified from images of a patient's brain (e.g., images obtained from an MRI system shown in FIG. 9). Alternatively, the lesion location may be determined using any other suitable technique including, but not limited to, determining the lesion location from one or more computed tomography (CT) scans and determining the lesion location from a pathological image.

Brain lesions mapped using the techniques described herein may result from any of a number of factors. For example, the brain lesion may be a naturally occurring lesion, e.g., caused by stroke, a permanent or temporary lesion intentionally created by a physician using techniques such as, radiofrequency ablation (RFA), non-invasive ultrasound, deep brain stimulation (DBA), transcranial magnetic stimulation (TMS), and the like, or a functional lesion created using any suitable technique, examples of which are known in the art.

The process then proceeds to act 120, where the intrinsic functional connectivity of the mapped lesion with the rest of the brain is assessed using human connectome data. In some embodiments, a functional connectivity map associated with the lesion location is determined based on the human connectome data. The functional connectivity map identifies one or more functional networks associated with the brain area in which the lesion is located. The one or more functional networks each include one or more brain areas functionally connected to the brain area in which the lesion is located. In some embodiments, a functional connectivity map representing the functional network(s) includes a plurality of correlation measures, with each correlation measure indicating a strength of functional connection between the brain area that includes the lesion location and respective brain areas in the functional network. In some embodiments, the correlation measure can indicate a type of correlation (e.g., positive or negative) and/or the strength of the correlation (e.g., strong, medium, or weak as represented by a numerical value or some other suitable metric).

In some embodiments, a functional connectivity map generated in accordance with the techniques described herein can include brain areas that are strongly correlated with the brain area in which the lesion is located. Strength of a functional connection be determined in any suitable way. For example, in some embodiments, one or more thresholds are used to determine the strength of a functional connection between two brain areas. In one implementation, it may be determined that the strength of the functional connection between two brain areas in the functional connectivity map is strong when the correlation measure associated with the functional connection between those two brain areas is 0.6 or higher (e.g., in the range of 0-1) for positive correlations and/or when the correlation measure is between −0.6 and −1 (e.g., in the range of −1-0) for negative correlations. It should be appreciated that a threshold value of 0.6 for determining whether a functional connection between two brain areas is strong is merely provided as an example, and another threshold value or values may alternatively be used.

In other embodiments, the functional connectivity map itself may only include brain areas that are associated with correlation measures above a threshold value. In such embodiments, determining whether there is a strong functional connection between two brain areas is simplified to a determination of whether the two brain areas are both included in the functional connectivity map.

In some embodiments, the functional connectivity map can be used to determine a likelihood that the brain lesion is causing a patient's symptoms. In an exemplary scenario, the patient may be exhibiting visual hallucinations. These symptoms are known to be generated by the extrastriate visual cortex. In some embodiments, the probability that a brain lesion located in another area of the brain is causing these symptoms is determined based on the functional connectivity of the brain area that includes the lesion location and the particular brain area(s) known to cause the symptoms (e.g., the extrastriate visual cortex).

In some embodiments, determining whether a lesion is causing particular symptom or symptoms comprises determining whether the particular brain areas(s) known to cause the symptoms is included in the set of brain areas in the functional connectivity map which also includes the brain area within which the lesion is located. For example, when it is determined that a functional connectivity map that includes the brain area of the lesion location, does not include the brain area known to cause the observed patient symptoms, or when the area known to cause the observed patient symptoms is included in the functional connectivity map, but only has a weak correlation measure between that area and the brain area of the lesion location, it may be determined that the brain lesion is not causing the patient's symptoms Conversely, it may be determined that the brain lesion is likely causing the patient's symptoms when there is a strong functional connection between the brain area including the lesion location and the brain area(s) known to cause the patient symptoms. In some embodiments, a brain lesion that is not causing the patient's symptoms can be referred to as an incidental lesion.

In some embodiments, a percent probability that the brain lesion is causing the patient's symptoms may be computed, based on the correlation measures associated with functional connections between brain regions. For example, a stronger correlation measure or higher value of the correlation measure can indicate a higher probability that the brain lesion is causing the patient's symptoms and vice versa. It will be appreciated that the percent probability may be computed in a number of ways without departing from the scope of the disclosure.

As described above, negative correlations or anti-correlations between the lesion location and the specific brain region(s) can also be taken into account in making determinations regarding whether the patient's symptoms are caused by the brain lesion. The inventors have recognized that functional connectivity maps provide insight into negative correlations (in addition to positive correlations) that can be useful in determining functional effects of the brain lesion because the brain lesion can be negatively correlated with particular brain area(s) involved with patient's symptoms.

According to another aspect, in addition to being able to determine whether the brain lesion is causing known symptoms of the patient, the lesion network mapping technique can be used to determine a measure (e.g., a probability) that each of a plurality of symptoms are likely to be caused by the brain lesion based on its location in the brain. For example, based on the location of the brain lesion, a list of most likely symptoms and/or disorders likely to be caused by the brain lesion can be generated. In some embodiments, the functional connectivity map associated with the lesion location is determined based on the human connectome data, as described above. The functional connectivity map includes a number of brain areas functionally connected to the brain lesion, with neural dysfunction in each of these brain areas contributing to one or more symptoms. The likelihood of the brain lesion causing these symptoms may then be determined based on the correlation measures associated with the brain areas functionally connected to the brain area that includes the location of the brain lesion. For example, based on the correlation measure associated with each brain area, a percent probability that the brain lesion is expected to cause symptoms associated with the brain areas is computed. The output of this process may be a list of symptoms that, based on the functional connectivity data, may be caused by a brain lesion in the brain area in which the brain lesion being interrogated is observed, and the percent probability for each of the symptoms. For example, for a patient whose brain lesion is caused by a stroke, the list can indicate that the patient has an 85% chance of developing post stroke pain (because the brain area responsible for generating pain symptoms is strongly correlated with the lesion location), a 40% chance of developing dystonia (because the brain area responsible for generating symptoms of dystonia is medium or "not as strongly" correlated with the lesion location), and a 1% chance of developing delusions (because the brain area responsible for generating symptoms of delusion is weakly correlated with the lesion location). In some embodiments, based on this list, a determination can be made that the brain lesion is not likely contributing to and/or causing the patient's symptoms of delusion, for example.

In some embodiments, based on the determination that the patient has an 85% chance of developing post stroke pain, a clinician can better plan for the patient's recovery by engaging the patient in appropriate medication trials, rehabilitation, and or other treatment strategies.

Referring back to FIG. 1, after the functional network map is generated, the process proceeds to act 130, where at least some aspects of the identified functional networks are displayed on an image of the patient's brain. Additionally or alternatively, one or more functional network targets may be identified in act 130, and the one or more functional network targets may be displayed on image of the patient's brain or the functional network targets may be identified in some other way including, but not limited to, providing coordinates of the functional network targets in any suitable coordinate system. In some embodiments, the functional network targets can include treatment targets (e.g., brain regions that may be the focus of pharmaceutical and/or other treatment, such as neuro stimulation treatment).

In some embodiments, the type and strength of the correlations between the brain area including the location of the brain lesion and different brain areas can also be displayed on the image of the patient's brain. For example, positive correlations can be displayed in warmer colors and negative correlations can be displayed in cooler colors. Also, stronger correlations can be displayed in darker colors and weaker correlations can be displayed in lighter colors. It will be appreciated that other ways to depict the type and strength of the correlations can be used without departing from the scope of this disclosure.

In some embodiments, the list of symptoms described above and the associated percent probability for each symptom may also be displayed in a tabular or other display format.

A non-limiting example providing experimental validation of the process of FIG. 1 is now described. In the experiment, cases of peduncular hallucinosis were identified from either local cases or from reports in the medical literature. Consent was obtained for the local cases according to the Declaration of Helsinki and the study was approved by the Partners Human Subjects Institutional Review Board. Cases from the literature were identified through a systematic search of pubmed.org with search terms of 'peduncular hallucinosis' or 'Lhermitte's hallucinosis'. The search was limited to articles in English, although an exception was made for historical French articles. Inclusion criteria included patients with predominantly visual hallucinations presumed to have been caused by a focal intraparenchymal lesion restricted to the brainstem or diencephalon, as demonstrated by imaging or anatomic examination. Exclusion criteria included: (i) co-occurring cortical lesions; (ii) lesions of the direct visual pathway; (iii) extrinsic compression injuries without a clearly delineated intra-parenchymal lesion; (iv) the presence of obvious competing etiologies for the hallucinations (e.g. a patient with comorbid psychosis or prior hallucinations from psychiatric disease, alcoholism, drug abuse or a suspected pharmacologic or metabolic cause); or (v) poor image resolution such that lesion boundaries could not be delineated. Twenty-three cases of peduncular hallucinosis with identifiable causative brain lesions (mean age 61+/−19 years, range 17-85) were selected for further analysis including three local cases and twenty cases from the medical literature.

Investigation of the networks associated with peduncular hallucinosis lesions involved three steps: (i) the volume of each of the twenty three lesions was transferred to a reference brain; (ii) the lesion volume was used as a seed region of interest in a resting state functional connectivity MRI analysis that used normative data; and (iii) the resulting network associated with each lesion volume was thresholded and overlaid across lesions to identify common sites of network overlap. For Step (ii), the full 3D lesion location was used as the seed region of interest for local cases, while a 2D slice or slices (i.e. non-expanded) were used for the previously published peduncular hallucinosis cases. The blood oxygen level-dependent signal for each lesion was an average of all voxels contained in the lesion volume. The resting state functional connectivity MRI data set included 98 healthy right-handed subjects (48 male subjects, age 22+/−3.2 years), part of a larger publically available data set. Subjects completed one or more resting state functional connectivity MM scans during which they were asked to rest in the scanner with their eyes open.

Mapping Lesions to a Reference Brain

Each of the lesions from the three local cases was mapped in three dimensions using simultaneous axial, coronal and sagittal views. Lesions from the twenty published figures were traced in the two-dimensional plane(s) in which they were displayed, using neuroanatomical landmarks to accurately transfer the lesion location onto the template brain. To identify areas of lesion overlap, 2D lesions from figures were extended by 2 mm perpendicular to the plane in which they were displayed to more closely approximate natural 3D lesion contours. A 2 mm extension was selected due to easy replication by others and to conservatively balance the risk of creating spurious sites of overlap versus missing sites of overlap relative to the actual 3D lesion shape. A more liberal lesion extension of 4 mm was also included for comparison. All lesions were mapped true to their laterality and areas of overlap were displayed using MRIcron.

Assessing Functional Connectivity

Resting state functional connectivity MRI data were processed in accordance with the strategy of Fox M D, Snyder A Z, Vincent J L, Corbetta M, Van Essen D C, Raichle M E. *The human brain is intrinsically organized into dynamic, anticorrelated functional networks. Proc Natl Acad Sci USA* 2005; 102: 9673-8 as implemented in Van Dijk K R, Hedden T, Venkataraman A, Evans K C, Lazar S W, Buckner R L. *Intrinsic functional connectivity as a tool for human connectomics: theory, properties, and optimization. J Neurophysiol* 2010; 103: 297-321, including global signal regression.

Each of the twenty three individual lesion-seeded resting state functional connectivity MRI network maps was thresholded at a t-value of +/−4.25 (P<0.00005, uncorrected). After applying this statistical threshold, the resulting twenty three binarized resting state functional connectivity MRI network maps were overlapped to identify regions of shared positive and negative correlation, masked using a whole-brain template.

An a priori region of interest covering the predicted location of network overlap in peduncular hallucinosis was selected from the Harvard Oxford Atlas distributed with FSL (lateral occipital cortex, inferior division, threshold of 50). This region was selected because it provided the best fit for the coordinates and Brodmann areas previously identified in the generation of release hallucinations.

In addition to identifying sites of network overlap, the experiment also sought to determine if lesion-based network results were specific to the actual lesion locations and not due to limitations in functional MRI spatial resolution, such that any subcortical lesion in the brainstem or thalamus could produce similar findings. To address this question the lesion network mapping was repeated with the same twenty three peduncular hallucinosis lesion masks in terms of volume, but the location of the lesion was randomized to anywhere within the brainstem or thalamus, repeated on 100 iterations. The inter-lesion distance and degree of lesion overlap was kept similar to that of the original lesions (lesion overlap of 6+/−2). Lesion volume was converted to a cube with automated morphing of the lesion shape to ensure that all voxels fell within the brainstem/thalamus mask. Network results from the actual lesions were compared to that of the randomized lesions using a voxel-wise Liebermeister test. This statistical approach is commonly referred to as voxel-based lesion symptom mapping and can identify voxels significantly more likely to relate to a particular lesion-induced symptom. The difference in this experiment was that the approach was applied towards lesion networks rather than just lesion locations. Voxels affected in <10% of cases were ignored and the resulting Z-maps were thresholded at a false discovery rate (FDR)-corrected P<0.05. This analysis was performed using nonparametric mapping software available at Mccausland Center for Brain Imaging, University of South Carolina, Columbia, S.C.

The voxel-wise Liebermeister test was used to assess whether (i) network overlap from actual lesions is greater than that of randomized lesions within the a priori region of interest; and (ii) network results preferentially localize to the a priori cortical region of interest relative to other cortical regions. The latter analysis compared the average voxel intensity (Z-score resulting from the voxel-wise Liebermeister test) in the a priori cortical region of interest to that of all other cortical areas from the Harvard Oxford Atlas (45 other regions, with right and left sides considered separately).

For both the lesion and lesion network mapping, coordinates of local maxima were identified using the cluster algorithm in FSL (Oxford, UK, minimum cluster size of two voxels, 15 local maxima per cluster, minimum distance between maxima of 10 mm). For the lesion analysis, clustering was performed on the lesion overlap image. For the lesion networks, clustering was performed on the Z-score maps resulting from the voxel-wise Liebermeister test comparing actual to randomized lesion networks. To account for the possibility that global signal regression confounded the ability to interpret anti-correlations, the analysis was repeated using an alternative method—anatomical CompCor implemented in the Conn toolbox.

Age may impact the strength of functional connectivity. The analysis described herein included patients with brain lesions that were older than the control cohort from which the normative functional connectivity MRI data were derived (61+/−18.7 years versus 22+/−3.2 years). To account for age differences, the analysis was repeated using functional connectivity data from a healthy older adult cohort (n=56, age 70.3+/−4.4 years) derived from the Harvard Brain Aging Study.

A quantitative comparison of the network results from the local cases in which 3D lesions were used for the functional connectivity analysis, relative to a single 2D slice taken from the center of the lesion was performed. This analysis was undertaken to assess the validity of using 2D slices to represent 3D lesions, which was done for the literature-derived lesions. A spatial correlation coefficient was used to quantify the similarity between network results.

Figure 2:
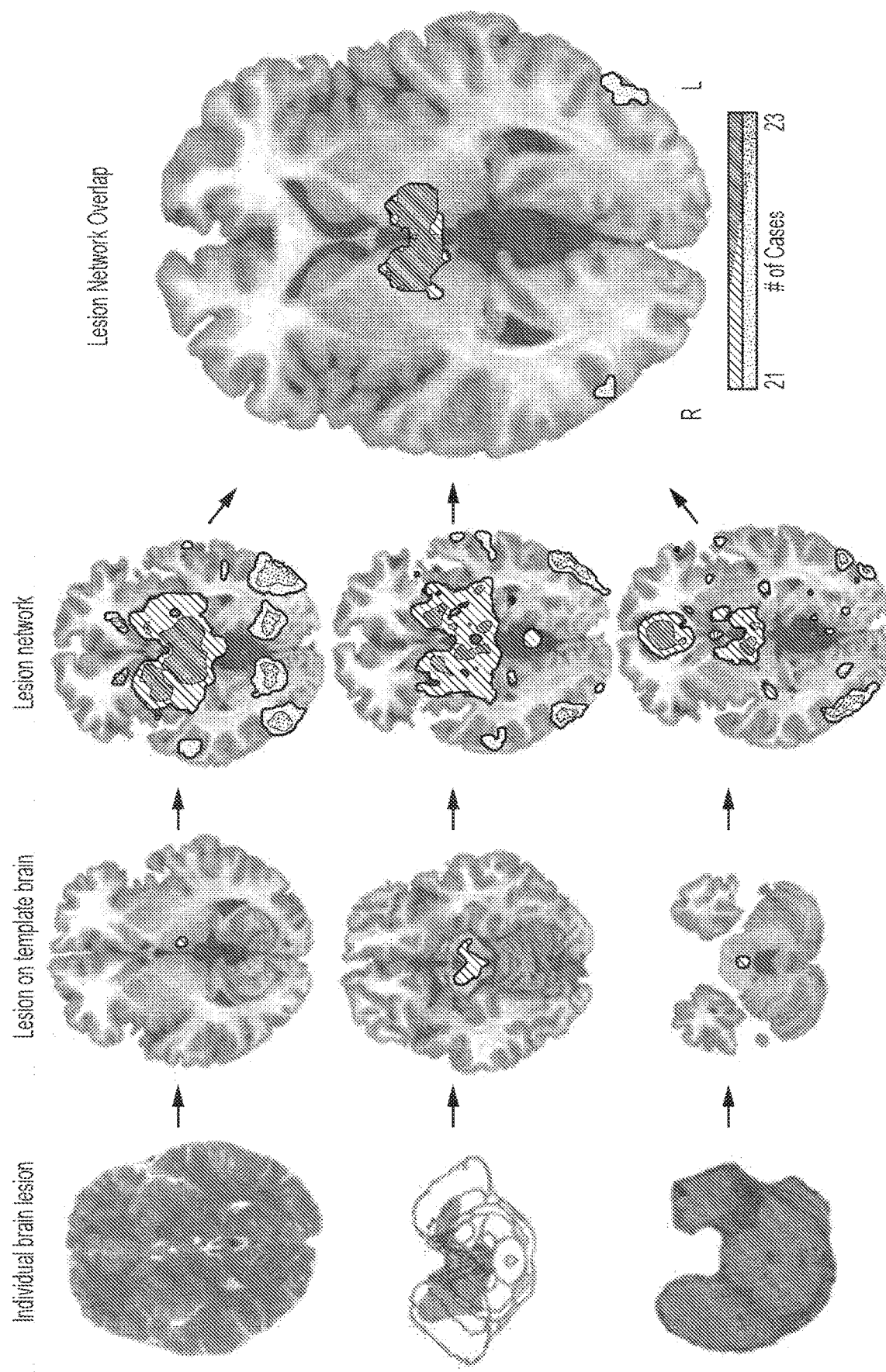
FIG. 2 illustrates a lesion network mapping process in accordance with some embodiments.

FIG. 2 illustrates the lesion network mapping method used in the above-described experimental validation in accordance with some embodiments. Twenty-three lesions resulting in peduncular hallucinosis were identified, three of which are illustrated in the leftmost column (column 1) of FIG. 2. The lesions were mapped to a reference brain as shown in column 2 of FIG. 2. The brain network associated with each lesion was identified using resting state functional connectivity data from a large cohort of normal subjects as shown in column 3 of FIG. 2. Positive correlations with the lesion are shown in hot colors while negative correlations (anticorrelations) are shown in cool colors. Networks common to at least 21 of 23 lesions were identified by overlapping the lesion-based networks of column 3 as shown in the rightmost column of FIG. 2.

The same methods used in the functional network analysis of peduncular hallucinosis lesions, discussed above and shown in FIG. 2, was repeated for three additional syndromes. Using lesion and lesion network data from all four conditions, a between-group analysis was performed using a voxel-wise Liebermeister test to assess whether the lesions and\or lesion networks could segregate between lesion syndromes (e.g. peduncular hallucinosis lesions and lesion networks compared to the other three conditions as 'controls').

Discussion of Experimental Results

Figure 3:
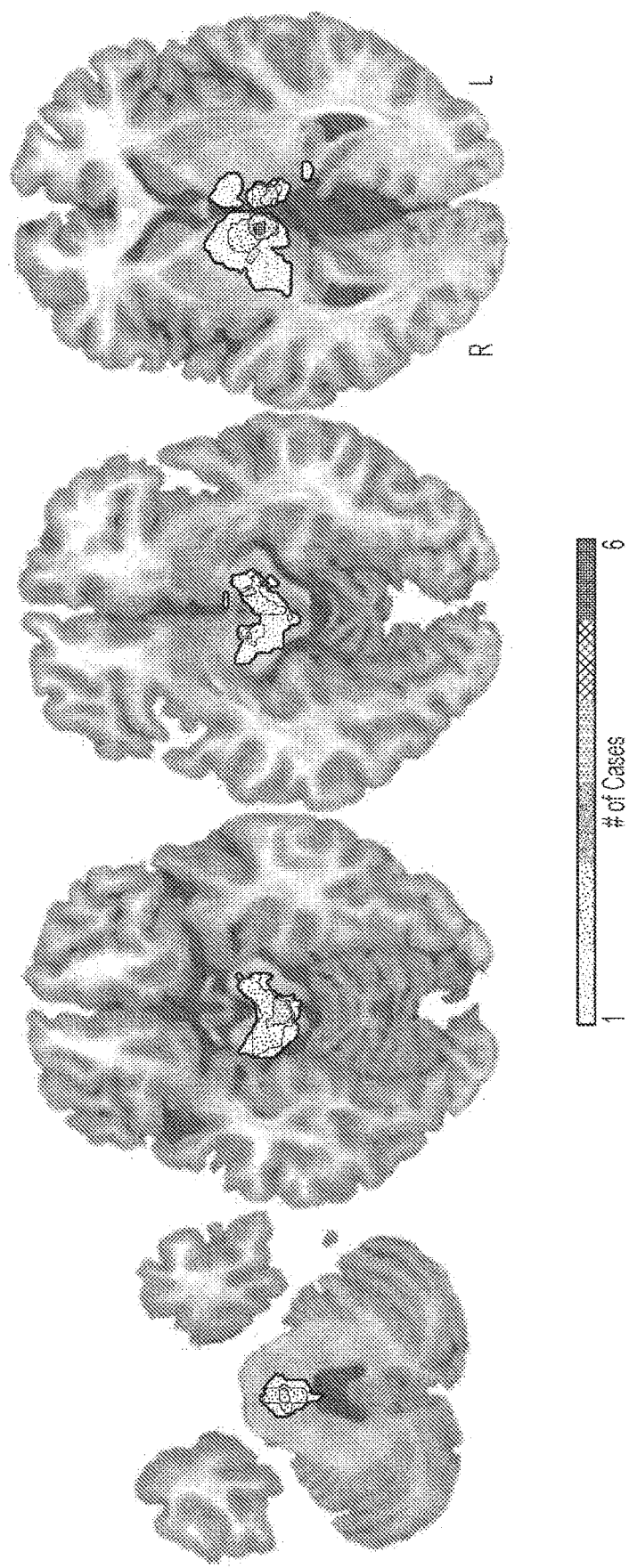
FIG. 3 shows results of a conventional lesion location mapping technique.

Following the conventional approach for relating symptoms to brain lesion location, each lesion was mapped to a reference brain and sites of lesion overlap were identified. FIG. 3 shows the results of a conventional lesion mapping approach to identify areas of overlap between lesion sites across patients. Areas of overlap among the twenty-three peduncular hallucinosis lesions are shown (from left to right) in the pontine tegmentum, paramedian mesencephalic tegmentum, substantia nigra pars reticulata and intralaminar/paramedian thalamus. The color scale indicates the number of overlapping lesions. Of twenty-three lesions, the maximum overlap was six cases (26%), indicating marked heterogeneity in lesion location. The site of maximum overlap was the right central thalamus (intralaminar and paramedian nuclei, n=6). Sites of maximum overlap were similar when extending the 2D lesions by 4 mm rather than 2 mm.

Analogous to viewing overlap at the lesion sites, overlap in lesion-based resting state networks was assessed in accordance with some embodiments. In contrast with the low overlap in lesion location (26%) discussed in connection with the conventional lesion mapping approach of FIG. 3, overlap in lesion-based networks was high (>90%) for both positive and negatively correlated networks. FIG. 4A shows areas of negative correlation (anticorrelation) in the overlap in lesion-based resting state networks, whereas FIG. 4B shows areas of positive correlation.

As shown in FIG. 4A, twenty-two of the twenty-three lesions had a significant network anticorrelation (negative correlation) with the extrastriate visual cortex within the a priori defined region of interest (outlined in FIG. 4A). Twenty-one of these lesions overlapped at the same location within this region of interest and an additional lesion had significant anticorrelation within this region, but at a site that did not overlap with the others. Using a slightly lower threshold, overlap in anticorrelated networks included regions in auditory and somatosensory association cortex, which is of interest given that hallucinations in peduncular hallucinosis can be multimodal. The Montreal Neurological Institute (MNI) coordinates of the axial slices shown in FIG. 4A are from left to right: −2, 0, 2, 4, and the MNI coordinates of the axial slices shown in FIG. 4B are from left to right: −13, −8, 0, 6.

The specificity of the primary finding, that lesions causing peduncular hallucinosis show network anticorrelation with extrastriate visual cortex was also evaluated by comparing network overlap in the a priori region of interest from actual lesions relative to randomized lesions using a voxel-wise Liebermeister test. This analysis showed significantly stronger network results for the actual lesions, with a peak level of significance of $P<10^{-5}$ which withstood correction for false discovery rate (<1%). Comparison of average voxel intensity from the cortical region of interest relative to all other cortical regions showed that these network findings were specific to the a priori region of interest (P<0.01).

The finding of anticorrelation in the extrastriate visual cortex was present after re-analyzing the data using an alternative algorithm that avoids global signal regression. When repeating the analysis using an older adult cohort that more closely matched the age of peduncular hallucinosis patients, the extrastriate anticorrelation was present irrespective of age. Finally, networks resulting from 2D versus 3D lesions were nearly identical, with a spatial correlation coefficient of 0.96, supporting the validity of the lesion networks derived from the literature.

Figure 5:
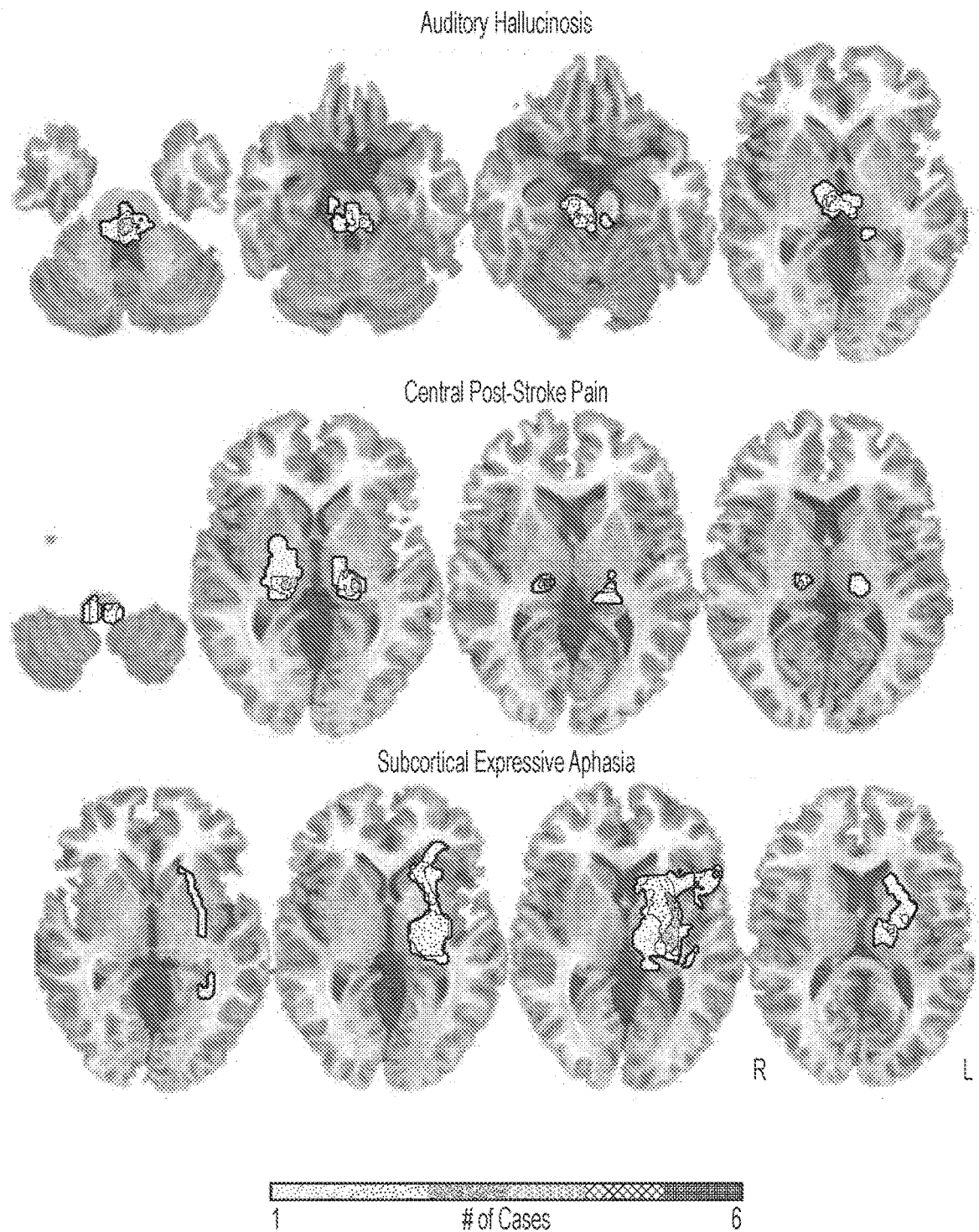
FIG. 5 shows results of applying a lesion network mapping process to lesions associated with auditory hallucinosis, central post-stroke pain, and subcortical expressive aphasia in accordance with some embodiments.

To determine whether lesion network mapping is generalizable beyond the application shown for peduncular hallucinosis, the lesion network mapping technique described herein was applied to three additional clinical syndromes: auditory hallucinosis, central post-stroke pain, and subcortical expressive aphasia, with the results shown in FIG. 5. As in peduncular hallucinosis, there were relatively low levels of overlap in lesion location using a conventional lesion mapping technique [auditory hallucinosis 3/15 (20%), central poststroke pain, 6/23 (26%), and subcortical expressive aphasia 5/12 (42%)]. However, an analysis based on lesion-based networks in accordance was some embodiments showed a high degree of overlap in the cortical region of interest hypothesized to be involved in symptom expression: superior temporal gyrus in auditory hallucinosis (88%), posterior insula in central post-stroke pain (78%), and Broca's area in subcortical expressive aphasia (100%).

Figure 6:
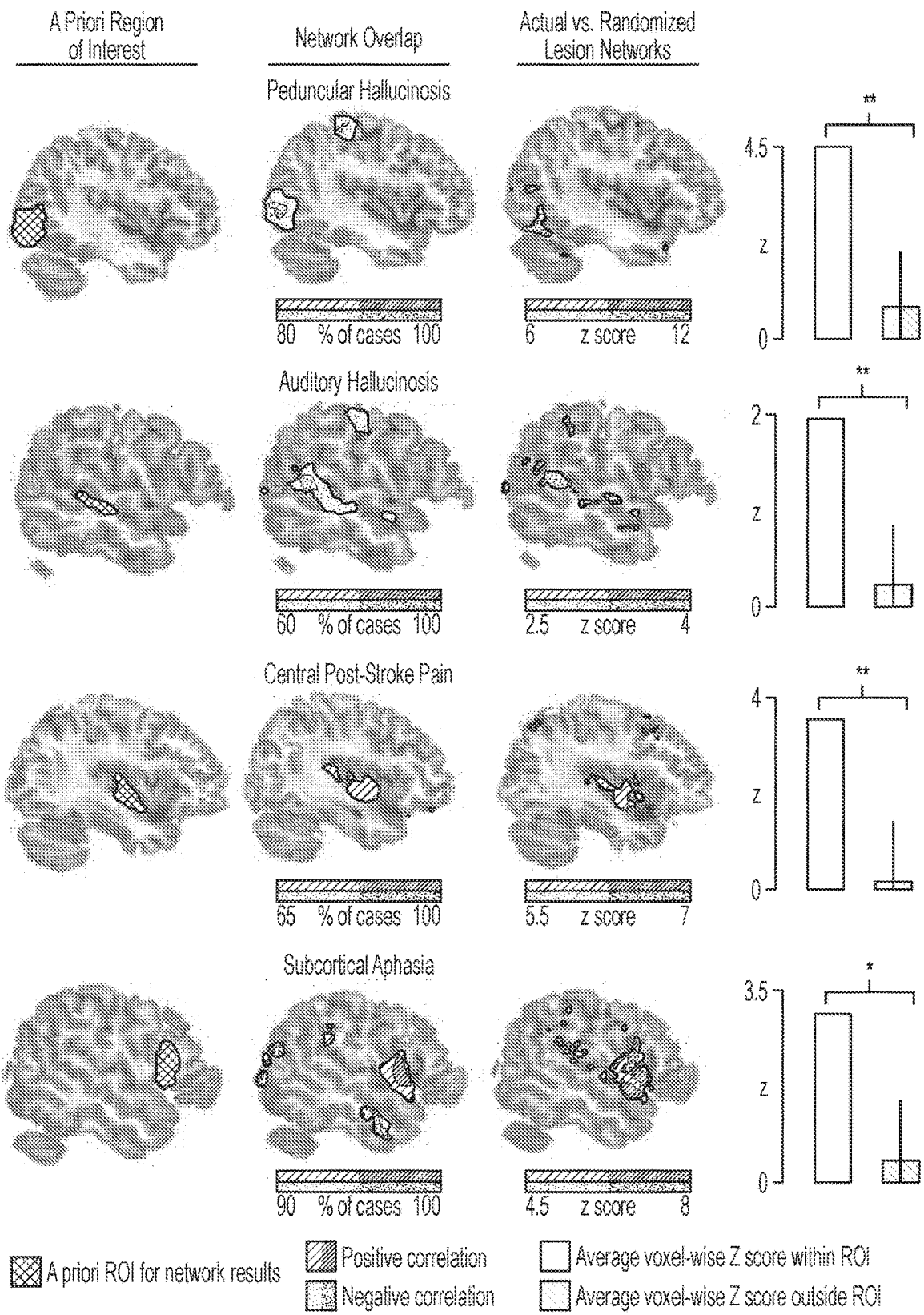
FIG. 6 shows a summary of lesion network mapping results for different medical conditions in accordance with some embodiments.

FIG. 6 summarizes the lesion network mapping results across all four conditions. The leftmost column (column 1) shows the hypothesized site of network overlap for each lesion syndrome, which was used to select regions of interest (ROIs) for the autocorrelation analysis, as described above. Column 2 shows the network overlap results, with positive correlations displayed in warmer colors and negative correlations in cooler colors. Column 3 shows the results of the voxel-wise Liebermeister test that compared network overlap from actual lesions relative to that of randomized lesions. The bar graph on the far right shows quantitative data supporting the specificity of the network overlap in the a priori cortical region of interest relative to all other cortical regions, derived from the voxel-wise Liebermeister results. For the bar graphs, *P<0.05, **P<0.01.

For all four conditions, network overlap for actual lesions significantly exceeded network overlap from randomized lesions within the a priori region of interest ($P<10^{-4}$). Moreover, as shown in FIG. 5, lesion networks localized to the a priori region of interest more than other cortical regions for each syndrome (P<0.05). These results were consistent across different statistical approaches including the voxel-wise Liebermeister test (FIG. 6), a simple t-test, and a subtraction analysis.

Figure 7A:
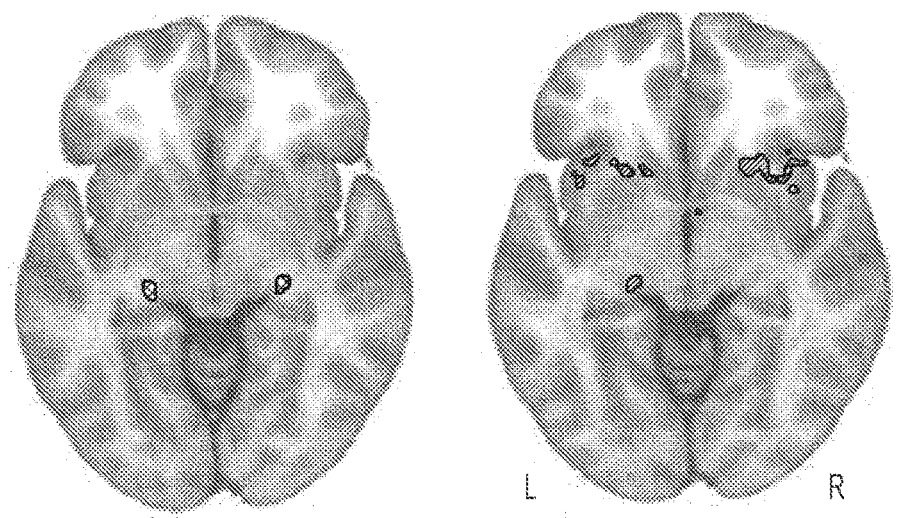
FIGS. 7A, 7B and 7C show correlations between brain regions outside of an expected brain region of interest and lesions in different syndromes in accordance with some embodiments.
Figure 7B:
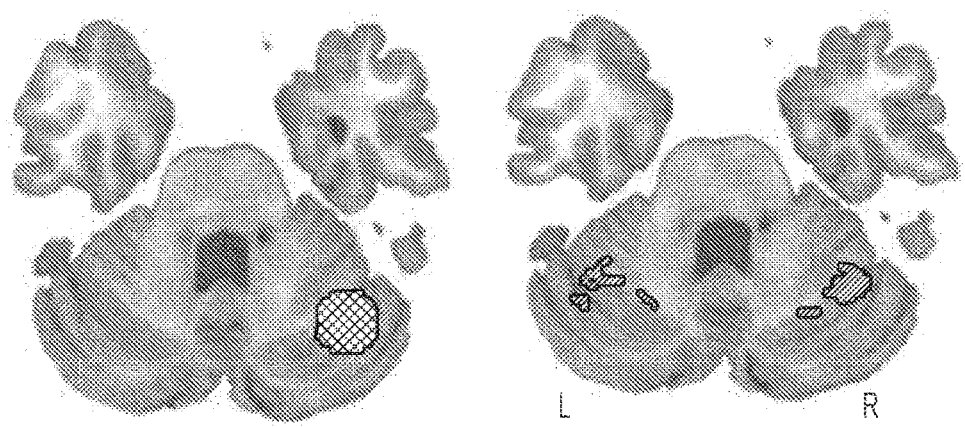
Figure 7C:
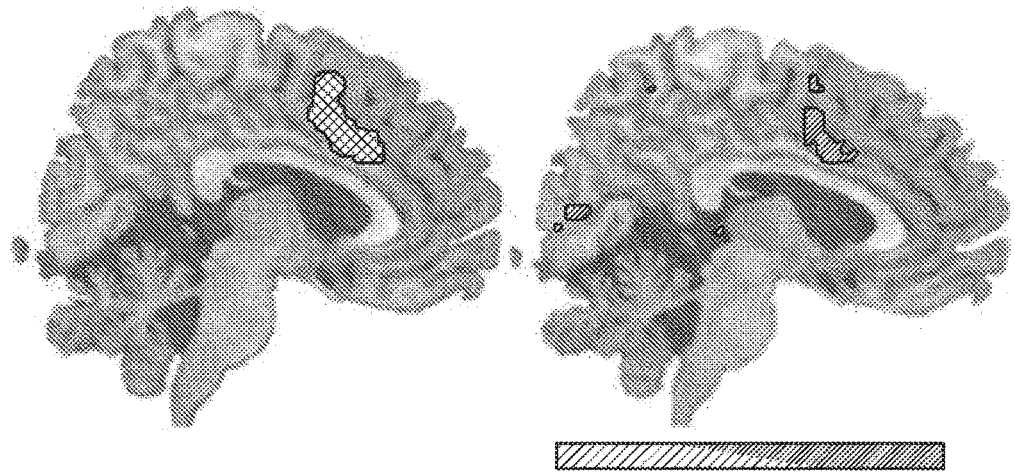

In addition to testing the a priori hypotheses discussed above, surprisingly it was found that significant network results also occurred in other regions outside the a priori region of interest defined for each syndrome. FIGS. 7A-7C illustrate these unexpected results. The left column shows a particular brain region and the right column shows areas that are positively correlated with syndrome lesions. All displayed voxels represent Z-scores from a voxel-wise Liebermeister test, significant at a false discovery rate of 5% or greater. The color bar minimum and maximum values show Z-scores of 7-9 for FIG. 7A, 3.5-5 for FIG. 7B, and 4-6 for FIG. 7C.

FIG. 7A shows that peduncular hallucinosis lesions are positively correlated with the lateral geniculate nucleus. FIG. 7B shows that subcortical aphasia lesions are positively correlated with the right lateral cerebellum in a region previously implicated in language. FIG. 7C shows that central poststroke pain lesions are positively correlated with the anterior cingulate cortex/medial prefrontal cortex, a node of the pain matrix identified in a meta-analysis of central pain functional MRI studies.

Figure 8:
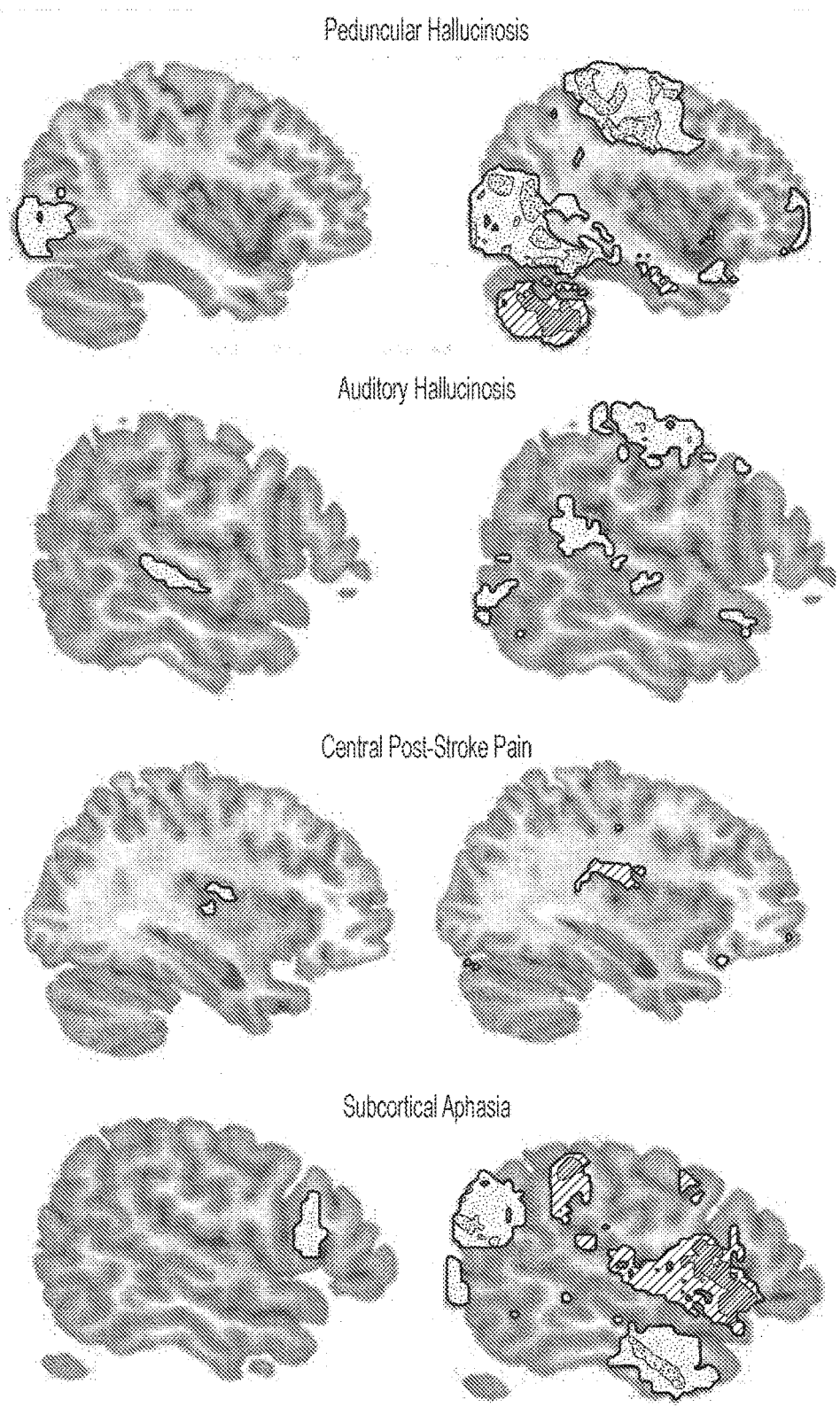
FIG. 8 shows results of mapping lesion networks between lesion syndromes in accordance with some embodiments.

It was also determined whether lesion networks could segregate between lesion syndromes better than the lesion locations themselves. FIG. 8 shows between-syndrome lesion network mapping results. Using lesion location alone there were no voxels that significantly associated with one lesion syndrome compared to the other three syndromes. In contrast, as shown in FIG. 8, comparison of lesion networks showed voxels significantly associated with each individual lesion syndrome using the same statistical threshold. Further, voxels significantly associated with each syndrome were located within the a priori cortical region of interest.

As shown in FIG. 8, voxel-based lesion-symptom mapping of the lesions did not segregate between lesion syndromes using a false discovery rate of 5%. In contrast, applying the same statistical approach there were voxels that segregated between lesion syndromes. The color scale denotes a voxel-wise Z-score from a Liebermeister test; 2.5 is statistically significant with a false discovery rate of 5%; 6 is significant at both a false discovery rate <1% and at P<0.01 after applying Bonferroni correction for multiple comparisons.

The experimental results described herein suggest that heterogeneous lesions causing similar symptoms share functional connectivity to specific brain areas implicated in symptom expression. In some cases this shared functional connectivity was based on positive correlations, whereas in other cases it was based on negative correlations. An important question is whether the sign of the functional connectivity predicts what type of remote functional effect will occur. For example, an anticorrelated relationship was observed between subcortical regions involved in release hallucinations and the cortical regions hypothesized to be 'released.' This includes extrastriate visual cortex in visual hallucinations and superior temporal gyrus in auditory hallucinations. Hypermetabolism has been demonstrated previously in both cortical regions in association with hallucinations raising the possibility that sites of anticorrelation predict sites of post-lesion hyperactivity.

Although there remains debate regarding the appropriate interpretation of anticorrelated brain networks, the finding that lesion sites are anticorrelated with cortical regions that become hyperactive following the lesion suggests that anticorrelations may reflect causal functional interactions. If negative correlation relates to post-lesion hyperperfusion, one would predict that positive correlation would relate to post-lesion hypoperfusion. Consistent with this notion, positive network connectivity between lesion location and language areas in subcortical aphasia corresponds to post-lesion hypoperfusion previously observed in these areas.

In contrast, post-stroke pain appears to deviate from this rule. Prior studies of central post-stroke pain have shown increased activity in the insula and anterior cingulate cortex, yet lesion network mapping showed positive correlation to these areas (see e.g., FIGS. 6 and 7C). One possible interpretation is that insula and anterior cingulate hypermetabolism observed in central post-stroke pain is not a direct effect of the lesion on these brain areas, but is the result of reorganization and neuroplasticity in these regions. Such an interpretation is consistent with the observation that central post-stroke pain has a delay in symptom onset of weeks or months after the injury, unlike other syndromes studied here. This could suggest that lesion network mapping predicts which remote brain areas are most likely to undergo compensation and reorganization over an extended time course, a process that likely differs from the immediate effects of the lesion on these same areas.

To validate the lesion network mapping approach described herein, an a priori region of interest already implicated in the symptom of interest was identified; however, interesting findings were also observed outside these regions. One example was the positive network overlap of peduncular hallucinosis lesions in the lateral geniculate nucleus (FIG. 7A). This finding raises the possibility that visual hallucinations stemming from insult to the direct visual pathway, variably termed "cortical release hallucinations" or "Charles Bonnet syndrome," share both clinical features and similar network localization to peduncular hallucinosis. Another example from subcortical aphasia was positive network overlap in the right lateral cerebellum (FIG. 7B). This finding fits well with an emerging literature on a role for the cerebellum in language, which includes cerebellum lesions causing aphasia. Together, these findings suggest that the lesion network mapping technique in accordance with some embodiments is capable of generating new unexpected findings and insights in addition to confirming existing hypotheses.

The techniques described herein for using lesion network mapping show that heterogeneous subcortical lesion sites for a syndrome are functionally connected to overlapping cortical areas implicated in symptom generation for that syndrome. Accordingly, lesion network mapping is an important addition to lesion methodology, expanding localization of symptoms from a focus on lesion sites, which often are poor predictors of symptoms, to lesion networks which are better predictors of such symptoms. Additionally, network localization may facilitate tailored modulation of connected networks using techniques like non-invasive brain stimulation with the therapeutic aim of alleviating clinical symptoms by targeting these areas for treatment.

Figure 9:
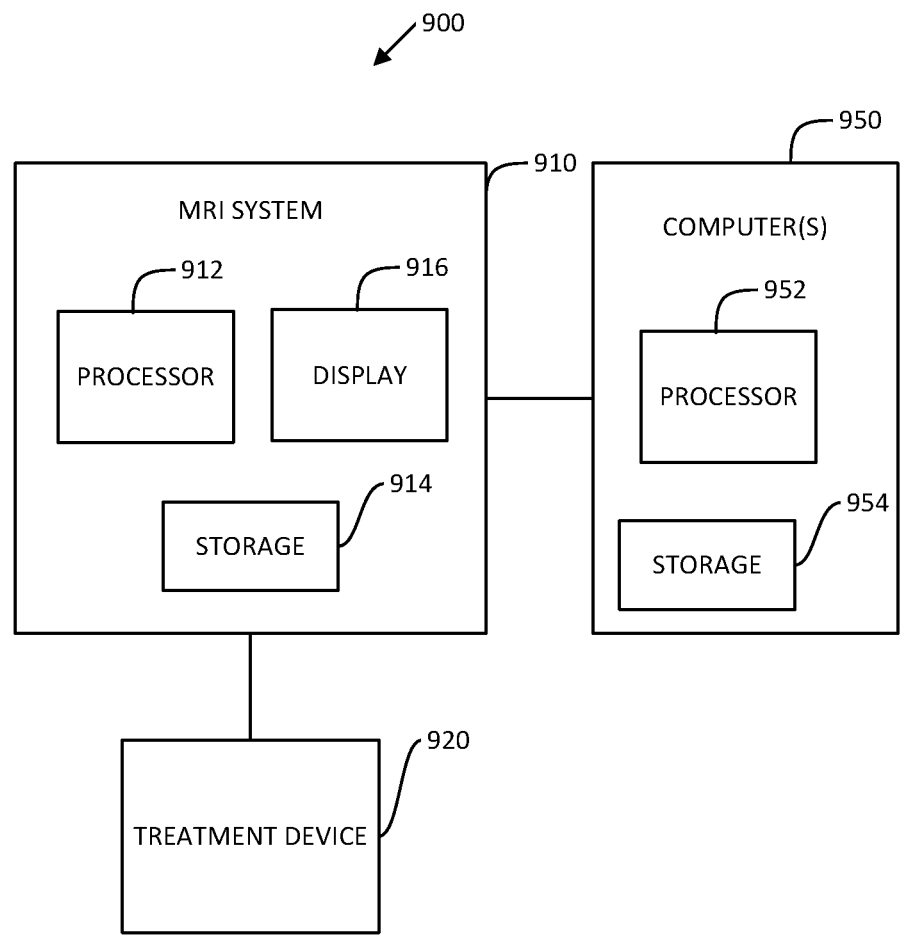
FIG. 9 shows a block diagram of a system that may be used to implement a lesion network mapping technique in accordance with some embodiments.

FIG. 9 illustrates an example system 900 within which one or more of the lesion network mapping techniques described herein may be implemented. System 900 includes MRI system 910 configured to acquire a plurality of structural images of at least a portion of a patient's brain. MRI system 910 also includes at least one processor 912 programmed to process one or more of the images acquired by MRI system 910 to perform at least a portion of a lesion network mapping process. MRI system 910 also includes storage device 914 configured to store the plurality of images acquired by MRI system 910 and/or results of the at least a portion of the lesion network mapping process performed by processor 912. In some embodiments, storage device 914 is configured to include a database/datastore of normative human connectome data that may be accessed by processor 914 to perform at least a portion of a lesion network mapping process. MRI system 910 further includes display 916 configured to output results of a lesion network mapping process. For example, display 916 may be configured to display one or more images of a patient's brain identifying one or more functional lesion networks and/or brain regions determined using one or more of the lesion network mapping processes described herein, and the type and strength of the correlations between the brain area that includes the lesion location and one or more of the brain areas in the identified functional lesion network(s). In some embodiments, a list of symptoms and associated percent probabilities generated by the lesion network mapping process, as discussed above, can also be displayed by display 916 or sent to an external electronic device (e.g, a smartphone) for display. Although shown as integrated with MRI system 910, in some embodiments, one or more of processor 912, storage 914, and display 916 may be implemented separate from MRI system 910 used to acquire the plurality of images, and these components may be operably connected to MRI system via one or more wired or wireless networks to enable communication between the components.

In some embodiments, the MRI system 910 is configured to acquire a plurality of structural images of at least a portion of a patient's brain, store the acquired images in storage device 914, and communicate the acquired images to at least one computer 950 (e.g., a server system). Computer 950 includes at least one processor 952 programmed to process the images acquired by MRI system 910 to identify locations of brain lesions from the images and/or to perform at least a portion of a lesion network mapping technique described herein. In such embodiments, the computer 950 may include a storage device 954 configured to store the images received from the MRI system 910. In some embodiments, the storage device 954 can store a database/datastore of the normative human connectome data. In other embodiments, the computer 950 may be communicatively coupled to an external database (not shown). The processor 952 accesses the database/datastore to perform at least a portion of the lesion network mapping process. The results of the lesion mapping process may be communicated back to the MRI system 910 to be displayed at display 916 or may be communicated to an external electronic device (e.g., a smartphone) for display.

Some embodiments are directed to a system that does not include an imaging (e.g., CT or MRI) scanner. In such embodiments, the system may include one or more computers 950 as shown in FIG. 9, which may be configured to receive one or more images on which the lesion mapping technique described herein is performed. For example, the one or more computers may implement a web service that receives as input over a network connection one or more CT or MRI images provided by a user. The one or more computers may process the image(s) using the lesion mapping technique described herein to perform one or more of (1) identifying a lesion in an image, (2) determining the location of the lesion, (3) determining a functional connectivity map associated with the brain area that includes the lesion location, and (4) determining, based, at least in part, on the functional connectivity map, a likelihood that the lesion is causing one or more patient symptoms.

As discussed above, some embodiments are directed to a method of determining a set of brain regions for treatment. Accordingly, example system 900 includes treatment device 920, which receives information about brain regions/networks to receive treatment. In some embodiments, treatment device 920 is a non-invasive brain stimulation device an example of which includes, but is not limited to, a transcranial magnetic stimulation (TMS) device. Treatment device 920 may be configured to provide treatment to one or more of the brain regions of a patient identified in the information received from MRI system 910 (or alternatively processor 912, when implemented separately from MRI system 910). In some embodiments, treatment device 920 is automatically configured for treatment based, at least in part, on the information received from MRI system 910. In other embodiments, treatment device 920 may be at least partially configured for treatment using a manual process.

As mentioned above, the lesion network mapping technique described herein provides an improvement over traditional lesion mapping techniques that require collection and analysis of functional neuroimaging data or specialized neuroimaging scans, which can be processor/memory intensive tasks. Accordingly, the lesion network mapping technique described herein provides a more computationally efficient technique for lesion mapping than prior approaches.

In some embodiments, the lesion network mapping technique can be used to make determinations regarding the likelihood of a patient benefiting from rehabilitation. Such information can be utilized, for example, by insurance companies or other entities to make assessments regarding reimbursement for a particular course of rehabilitation treatment.

In some embodiments, the lesion network mapping technique described herein can be used to provide information to pharmaceutical companies during testing of the efficacy of a pharmaceutical product under development. For example, brain areas responsible for generating symptoms that the drug is used to treat may be identified using the lesion network mapping technique. By determining that the drug is affecting the identified brain areas, a pharmaceutical company may be able to better determine that the pharmaceutical product is effective in treating particular symptoms In some embodiments, the lesion network mapping technique described herein allows for identification of treatment targets based on an overlap in the functional networks associated with multiple brain lesions. For instance, the lesion network mapping technique can be applied to generate functional connectivity maps for each lesion in a set of brain lesions (e.g., at a plurality of lesion locations). The functional connectivity maps (associated with the different lesion locations) can be analyzed to determine a treatment target. For example, a common brain area functionally connected to some or all of the multiple lesion locations may be identified as the treatment target.

In some embodiments, the lesion network mapping technique described herein can be used to identify patients that have brain tissue that can be saved following a stroke. The technique can identify whether the patient's symptoms and the symptom severity is appropriate for the brain lesion. For example, a patient that is exhibiting more symptoms than appropriate for the location of the brain lesion, may be identified as the patient who has additional brain tissue that can be saved, whereas a patient that exhibits symptoms associated only with or primarily with the brain areas in the functional connectivity map may not be a candidate for surgical procedures that save additional brain tissue. This identification can provide useful information to a clinician for making treatment decisions (e.g., whether to deliver tPA or another clot-busting therapy for stroke patients).

Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be considered as one or more controllers that control the above-discussed functions.

In this respect, it should be appreciated that one implementation of the embodiments of the present invention comprises at least one non-transitory computer-readable storage medium (e.g., a computer memory, a USB drive, a flash memory, a compact disk, a tape, etc.) encoded with a computer program (i.e., a plurality of instructions), which, when executed on a processor, performs the above-discussed functions of the embodiments. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. to modify elements does not by itself connote any priority, precedence, or order of one element over another or the temporal order in which acts of a method are performed. Such terms are used merely as labels to distinguish one element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

The invention claimed is:

1. A method of evaluating a brain lesion in a patient's brain, the method comprising:
   performing a lesion network mapping by using a computer processor to:
   group heterogeneously distributed lesions into a network, the network comprising lesions that result in a same clinical syndrome, and
   link, based on resting state functional connectivity data, the brain lesion to lesions of the network in remote brain areas having a recognized role in a behavioral expression of a symptom in common with a patient symptom,
   wherein the performing comprises determining, using the computer processor, based on human connectome data stored on at least one computer datastore in communication with the computer processor, at least one functional network associated with a location of the brain lesion identified in an image of the patient's brain, the at least one functional network including a plurality of brain areas functionally connected to the location of the brain lesion and a plurality of correlation measures, each of the correlation measures indicating a strength of a negative or positive functional connection between the location of the brain lesion and a respective brain area of the plurality of brain areas in the at least one functional network; and determining, by the computer processor, a probability that the patient symptom is caused by the brain lesion based on the correlation measures of the at least one functional network when there is a functional connection between the location of the brain lesion and at least one of the remote brain areas, wherein the functional connection comprises a correlation measure exceeding a threshold value for strength of a functional connection.

2. The method of claim 1, wherein the human connectome data comprises the resting state functional connectivity data.

3. The method of claim 2, wherein the resting state functional connectivity data comprises data regarding spontaneous fluctuations in brain activity in a resting state.

4. The method of claim 1, wherein the determining of the probability comprises:
   determining a corresponding brain area associated with the patient symptom;
   determining whether the corresponding brain area is included in the plurality of brain areas in the at least one functional network; and
   determining that the patient symptom is caused by the brain lesion when it is determined that the corresponding brain area is included in the plurality of brain areas in the at least one functional network.

5. The method of claim 4, further comprising:
   determining that the patient symptom is not caused by the brain lesion when it is determined that the corresponding brain area is not included in the plurality of brain areas in the at least one functional network.

6. The method of claim 1, wherein the determining of the probability comprises:
   for a first brain area of the plurality of brain areas, determining whether a correlation measure describing a strength of a functional connection between the first brain area and a brain area that includes the location of the brain lesion is greater than a threshold value, wherein the first brain area is associated with the patient symptom; and
   determining that patient symptom is caused by the brain lesion when the correlation measure describing the strength of the functional connection between the first brain area and the brain area that includes the location of the brain region lesion is greater than the threshold value.

7. The method of claim 1, wherein each of the plurality of correlation measures indicates a type of correlation between the location of the brain lesion and a respective brain area of the plurality of brain areas.

8. The method of claim 7, wherein the type of correlation comprises a negative correlation between the location of the brain lesion and the respective brain area.

9. A system comprising:
   a magnetic resonance imaging (MRI) system configured to acquire one or more images of a patient's brain;
   a database configured to store human connectome data comprising resting state functional connectivity data; and
   at least one computer communicatively coupled to the MRI system and the database, the at least one computer comprising a computer processor configured to perform acts of:
      receiving the one or more images from the MRI system;
      identifying a location of a brain lesion from the one or more images;
      performing a lesion network mapping to:
         group heterogeneously distributed lesions into a network, the network comprising lesions that result in a same clinical syndrome, and
         link, based on resting state functional connectivity data, the brain lesion to lesions of the network in remote brain areas having a recognized role in a behavioral expression of a symptom in common with a patient symptom,
         wherein the performing comprises determining, based on the human connectome data and the identified location of the brain lesion, a functional connectivity map associated with the location of the brain lesion, the functional connectivity map including a plurality of brain areas functionally connected to the location of the brain lesion and a plurality of correlation measures, each of the correlation measures indicating a strength of a negative or positive functional connection between the location of the brain lesion and a respective brain area of the plurality of brain areas in the functional connectivity map; and
      determining probability that the patient symptom is caused by the brain lesion based on the correlation measures of the at least one functional network when there is a functional connection between the location of the brain lesion and at least one of the remote brain areas, wherein the functional connection comprises a correlation measure exceeding a threshold value for strength of a functional connection.

10. The system of claim 9, wherein the resting state functional connectivity data comprises data regarding spontaneous fluctuations in brain activity in a resting state.

11. The system of claim 9, wherein the act of determining the probability comprises:
   determining a corresponding brain area associated with the patient symptom;
   determining whether the corresponding brain area is included in the plurality of brain areas in the functional connectivity map; and
   determining that the patient symptom is caused by the brain lesion when it is determined that the corresponding brain area is included in the plurality of brain areas in the functional connectivity map.

12. The system of claim 11, wherein the computer processor is further configured to perform an act of:
   determining that the patient symptom is not caused by the brain lesion when it is determined that the corresponding brain area is not included in the plurality of brain areas in the functional connectivity map.

13. The system of claim 9, wherein the act of determining the probability comprises:
   for a first brain area of the plurality of brain areas in the functional connectivity map, determining whether a correlation measure describing a strength of a functional connection between the first brain area and a brain area that includes the location of the brain lesion is greater than a threshold value, wherein the first brain area is associated with the patient symptom; and determining that the patient symptom is caused by the brain lesion when the correlation measure describing the strength of the functional connection between the first brain area and the brain area that includes the location of the brain lesion is greater than the threshold value.

14. The system of claim 9, wherein each of the plurality of correlation measures indicates a type of correlation between the location of the brain lesion and the respective brain area.

15. The system of claim 14, wherein the type of correlation comprises a negative correlation between the location of the brain lesion and a respective brain area of the plurality of brain areas.

16. The system of claim 9, wherein the computer processor is further configured to perform an act of:
displaying a percent probability that the patient symptom is caused by the brain lesion, wherein the percent probability is computed based on the plurality of correlation measures.

17. The system of claim 9, wherein the computer processor is further configured to perform an act of:
identifying, as targets for treatment, a set of one or more brain regions of the patient's brain that are predicted to be affected by the brain lesion.

18. The system of claim 9, wherein the strength of the negative or positive functional connection is represented numerically.

19. The system of claim 9, wherein the computer processor is further configured to perform an act of:
displaying on the one or more images of the patient's brain a positive or negative type and the strength of the negative or positive functional correlation between the location of the brain lesion and each of the plurality of brain areas that are functionally connected to the location of the brain lesion.

20. The method of claim 1, further comprising:
displaying a percent probability that the patient symptom is caused by the brain lesion, wherein the percent probability is computed based on the plurality of correlation measures.

21. The method of claim 1, further comprising:
identifying, as target sites for treatment, a set of one or more brain regions of the patient's brain that are predicted to be affected by the brain lesion.

22. The method of claim 1, wherein the strength of the negative or positive functional connection is represented numerically.

23. The method of claim 1, further comprising:
displaying on the image of the patient's brain a positive or negative type and the strength of the negative or positive functional correlation between the location of the brain lesion and each of the plurality of brain areas that are functionally connected to the location of the brain lesion.

\* \* \* \* \*